US011058557B2

(12) United States Patent
Tompkins

(10) Patent No.: US 11,058,557 B2
(45) Date of Patent: Jul. 13, 2021

(54) DIGITAL TO DEFINITIVE ORTHOTIC AND PROSTHETIC DEVICE MANUFACTURING SYSTEM AND METHOD

(71) Applicant: Hanger, Inc., Austin, TX (US)

(72) Inventor: Michael E. Tompkins, Austin, TX (US)

(73) Assignee: HANGER, INC., Austin, TX (US)

( * ) Notice: Subject to any disclaimer, the term of this patent is extended or adjusted under 35 U.S.C. 154(b) by 101 days.

(21) Appl. No.: 16/050,849

(22) Filed: Jul. 31, 2018

(65) Prior Publication Data

US 2018/0353308 A1  Dec. 13, 2018

Related U.S. Application Data

(63) Continuation of application No. PCT/US2017/015981, filed on Feb. 1, 2017.
(Continued)

(51) Int. Cl.
*A61F 2/60* (2006.01)
*A61F 2/80* (2006.01)
(Continued)

(52) U.S. Cl.
CPC .............. *A61F 2/5046* (2013.01); *A61F 2/50* (2013.01); *A61F 2/54* (2013.01); *A61F 2/583* (2013.01); *A61F 2/585* (2013.01); *A61F 2/60* (2013.01); *A61F 2/66* (2013.01); *A61F 2/7812* (2013.01); *A61F 2/80* (2013.01); *A61F 5/01* (2013.01); *B33Y 50/00* (2014.12); *B33Y 80/00* (2014.12); *A61F 5/0127* (2013.01);
(Continued)

(58) Field of Classification Search
CPC ......... G05B 2219/49007; A61F 2/5046; A61F 2/60; A61F 2/80
See application file for complete search history.

(56) References Cited

U.S. PATENT DOCUMENTS 4,134,159 A * 1/1979 Wilson
6,669,736 B2 * 12/2003 Slemker .................. B29C 41/20
623/32
(Continued)

OTHER PUBLICATIONS

Search Report for International Application No. PCT/US2017/015981, dated May 11, 2017, 14 pages.

*Primary Examiner* — Bruce E Snow
(74) *Attorney, Agent, or Firm* — Foley & Lardner LLP

(57) ABSTRACT

Systems and methods for creating custom-fit prosthetic devices, orthotic devices, and related medical devices via three-dimensional printing (3D printing) or additive manufacturing techniques are described. Through the described systems and methods, a residual limb or other body part of a patient is scanned and analyzed to determine measurements and characteristics of the residual limb. The measurements and characteristics of the residual limb are used to design a customized device for the residual limb. The customized device uses multiple different materials. For example, the customized device may use a first material for a frame and a second material for a liner, wherein the first material is more rigid than the second material. The customized device is fabricated using a three-dimensional printer that is capable of printing and bonding multiple different materials at the same time.

11 Claims, 6 Drawing Sheets

Related U.S. Application Data

(60) Provisional application No. 62/290,254, filed on Feb. 2, 2016.

(51) Int. Cl.
| | | |
|---|---|---|
| *A61F 2/50* | (2006.01) | |
| *A61F 5/01* | (2006.01) | |
| *B33Y 50/00* | (2015.01) | |
| *B33Y 80/00* | (2015.01) | |
| *A61F 2/54* | (2006.01) | |
| *A61F 2/58* | (2006.01) | |
| *A61F 2/66* | (2006.01) | |
| *A61F 2/78* | (2006.01) | |
| *B33Y 10/00* | (2015.01) | |
| *G05B 19/4099* | (2006.01) | |

(52) U.S. Cl.
CPC . *A61F 2002/505* (2013.01); *A61F 2002/5049* (2013.01); *A61F 2002/607* (2013.01); *A61F 2002/6614* (2013.01); *A61F 2002/7818* (2013.01); *A61F 2002/802* (2013.01); *B33Y 10/00* (2014.12); *G05B 19/4099* (2013.01); *G05B 2219/35134* (2013.01); *G05B 2219/49007* (2013.01)

(56) References Cited

U.S. PATENT DOCUMENTS

| | | | |
|---|---|---|---|
| 2005/0038522 A1* | 2/2005 | Helenberger | A61F 2/76 623/36 |
| 2006/0094951 A1 | 5/2006 | Dean et al. | |
| 2015/0142150 A1 | 5/2015 | Layman et al. | |
| 2015/0250715 A1 | 9/2015 | Adams et al. | |
| 2016/0074182 A1* | 3/2016 | Celebi | A61F 2/78 623/33 |

* cited by examiner

DIGITAL TO DEFINITIVE ORTHOTIC AND PROSTHETIC DEVICE MANUFACTURING SYSTEM AND METHOD

CROSS-REFERENCE TO RELATED APPLICATIONS

This application is a continuation of International Application No. PCT/US2017/015981, filed Feb. 1, 2017, which claims priority to U.S. Provisional Patent Application No. 62/290,254, filed on Feb. 2, 2016, each of which are incorporated herein by reference in their entirety and for all purposes.

TECHNICAL FIELD

The present application relates to orthotic device manufacturing systems and methods.

BACKGROUND

Three-dimensional printing and additive manufacturing (referred herein as "3D printing") has introduced many new manufacturing capabilities in various industries. For example, through 3D printing, it is possible to efficiently create rapid prototypes or various layered designs not easily feasible with conventional manufacturing. However, 3D printing is traditionally used with a limited range of materials, which may be weak and brittle. Additionally, 3D printing devices often are limited in the numbers and types of materials that can be used to manufacture devices.

SUMMARY

Various example embodiments relate to methods of manufacturing medical devices via 3D printing techniques and 3D printed medical devices. One such example embodiment relates to a method of manufacturing a medical device. The method includes receiving, by a manufacturing computing system, three-dimensional patient information related to a body part of a patient from a three-dimensional scanner. The method further includes forming, by the manufacturing computing system, a computer aided design model of the medical device based at least in part on the three-dimensional patient information. The method includes generating, by the manufacturing computing system, computer aided manufacturing instructions for the computer aided design model of the medical device, wherein the computer aided manufacturing instructions are formatted for a three-dimensional printer. The method further includes printing, by the three-dimensional printer, the medical device.

Another example embodiment relates to a prosthetic device. The prosthetic device includes a socket defining a cavity configured to receive a residual limb of a user, wherein the socket is formed by a three-dimensional printing process. The prosthetic device further includes a pylon coupled to the distal end of the socket by a threaded fastener. The prosthetic device includes a connection insert within the socket. The connection insert includes an internally threaded fastener aligned with a through hole in the socket, wherein the internally threaded fastener is structured to receive the threaded fastener thereby securing the pylon to the socket.

A further example embodiment relates to a connection insert for a prosthetic device. The connection insert includes a connection insert body. The connection insert further includes first, second, third, and fourth internally threaded fasteners coupled to the connection insert body. The connection insert body is configured to receive a threaded fastener thereby coupling a component to the prosthetic device. The connection insert body has an overall X-shape or U-shape.

These and other features, together with the organization and manner of operation thereof, will become apparent from the following detailed description when taken in conjunction with the accompanying drawings, wherein like elements have like numerals throughout the several drawings described below.

DETAILED DESCRIPTION

Referring to the figures generally, systems and methods for creating custom-fit prosthetic devices, orthotic devices, and related medical devices via three-dimensional printing (3D printing) or additive manufacturing techniques are described. For example, the described systems and methods may be used to fabricate prosthetic devices, cranial remolding orthosis devices, ankle-foot orthosis devices, upper and lower extremity prosthetic devices, shoe inserts, and the like. Through the described systems and methods, a residual limb or other body part of a patient is scanned and analyzed to determine measurements and characteristics of the residual limb. The measurements and characteristics of the residual limb are used to design a customized device for the residual limb. The customized device uses multiple different materials. For example, the customized device may use a first material for a frame and a second material for a liner, wherein the first material is more rigid than the second material. The customized device is fabricated using a three-dimensional printer that is capable of printing and bonding multiple different materials at the same time.

Figure 1:
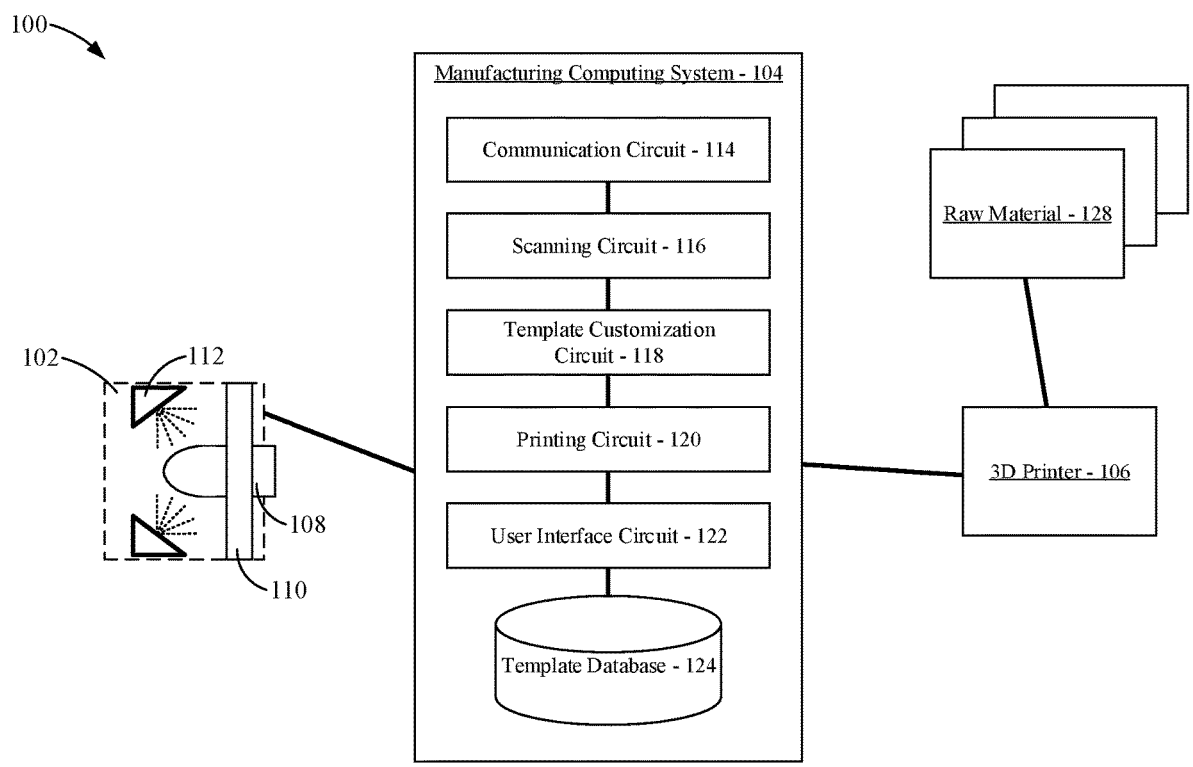
FIG. 1 shows a system for making a custom fit prosthetic or orthotic device according to an example embodiment.

Referring to FIG. 1, a system 100 for making a custom fit prosthetic or orthotic device is shown according to an example embodiment. The system 100 includes a 3D scanner 102, a manufacturing computing system 104, and a 3D printer 106. The 3D scanner 102 is structured to scan a residual limb 108 of a patient. The residual limb 108 may be, for example, a portion of an arm of the patient, a portion of a leg of the patient, or the like. The 3D scanner 102 includes a residual limb support 110. The residual limb support 110 secures the residual limb 108 of the patient in the 3D scanner 102 such that the motion of the residual limb 108 is limited during scanning. The residual limb 110 support is adjustable to accommodate different sizes and different types of residual limbs. The 3D scanner 102 includes at least one scanning device 112. The scanning device 112 may be a camera, an infrared camera, a laser, an ultrasonic sensor, a contact sensor, or the like. The scanning device 112 measures the geometry and size of at least a portion of the residual limb 108. In some arrangements, the scanning device 112 maps the portion of the residual limb 108 as a three-dimensional map. The three-dimensional map may be formed by a table of three-dimensional coordinates. In some arrangements, the scanning device 112 rotates about the residual limb 108 to measure the entirety of the portion of the residual limb 108.

The manufacturing computing system 104 is communicatively coupled to the 3D scanner 102 and the 3D printer 106. Generally, the manufacturing computing system 104 controls the operation of the 3D scanner 102 and the 3D printer 106. In some arrangements, the manufacturing computing system 104 is integrated with at least one of the 3D scanner 102 or the 3D printer 106. The manufacturing computing system 104 includes various circuits that control the operation of the manufacturing system 104, including a communication circuit 114, a scanning circuit 116, a template customization circuit 118, a printing circuit 120, and a user interface circuit 122.

The communication circuit 114 is structured to facilitate data communication to and from other devices, such as the 3D scanner 102 and the 3D printer 106. In some arrangements, data passing through the communication circuit 114 is encrypted. The data communication via the communication circuit 114 may be communicated directly between the manufacturing computing system 104 and other devices or via a network (e.g., the Internet). The communication circuit 114 may be structured to communicate via any combination of wired network protocols (e.g., Ethernet, USB, Thunderbolt, etc.) and wireless network protocols (e.g., WiFi, Bluetooth, CDMA, GSM, LTE, ZigBee, etc.).

The scanning circuit 116 is structured to control the operation of the 3D scanner 102. For example, the scanning circuit 116 can instruct the scanning device 112 to analyze the residual limb 108 based on an instruction received from a technician (e.g., via the user interface circuit 122). In doing so, the scanning circuit 116 may control the movement (e.g., rotation) of the scanning device 112 with respect to the residual limb 108. In some arrangements, the scanning circuit 116 transforms the information received from the scanning device 112 to a three-dimensional map file that is formed by a table of three-dimensional coordinates.

The template customization circuit 118 modifies a selected device template from the template database 124 based on the size and shape of the residual limb 108. The template database 124 stores design templates for various prosthetic and orthotic devices (e.g., prosthetic arms, prosthetic hands, prosthetic legs, orthotic inserts, etc.) that can be printed by the 3D printer 106. The templates stored in the template database 124 may be organized by type (e.g., arm, leg, foot, etc.) and size (e.g., by age, by height of the patient, by weight of the patient, etc.). In some arrangements, the template database 124 also stores add-on or additional features that can be added to a given orthotic or prosthetic template, such as capacitive touch features, lining styles, vacuum assist features, openings for sensors, and the like. The template customization circuit 118 is structured to allow a user to select a template of a device (e.g., via the user interface circuit 122) and to modify the template to fit the residual limb 108 based on the information received from the 3D scanner 102. The modified template is the design for the custom-fit orthotic or prosthetic device.

The manufacturing computing system 104 includes the printing circuit 120. The printing circuit 120 is structured to generate and send instructions to the 3D printer 106 (e.g., via the communication circuit 114). The printing circuit 120 generates the instructions from the design generated by the template customization circuit 118 by converting the design into tool path instructions (e.g., via computer-aided manufacturing (CAM) conversions) for the 3D printer 106. The instructions identify the print head path and the material needed to print each section of the device.

The manufacturing computing system 104 includes the user interface circuit 122. The user interface circuit 122 is structured to allow a user to interact with the manufacturing computing system 104. Accordingly, the user interface circuit 122 may include user output devices (e.g., a display, speakers, LEDs, lights, etc.) and user input devices (e.g., a keyboard, a mouse, a touchscreen display, etc.).

Still referring to FIG. 1, the system 100 includes the 3D printer 106. The 3D printer 106 is structured to print the device as instructed by the printing circuit 120 of the manufacturing computing system 104. In some arrangements, the 3D printer 106 is a large format 3D printer with a print area large enough to accommodate any printed prosthetic or orthotic device. The 3D printer 106 includes multiple print heads, wherein each head can print a different one of the raw materials 128. The different print heads may include any combination of stereolithography print heads, digital light processing print heads, fused deposition modeling print heads, selective laser sintering print heads, selective laser melting print heads, electronic beam melting print heads, and/or laminated object manufacturing print heads. The raw materials 128 may include any combination of Acrylonitrile Butadiene Styrene (ABS), Polylactic Acid (PLA), Nylon, polyethylene co-polymer, Thermoplastic elastomer (TPE), polypropylene, thermoplastic polyurethane (TPU), rubber-elastomeric polymer, etc. These materials can also be formulated with glass fiber, carbon nanotubes, carbon fiber, Poly Vinyl Alcohol (PVA), and the like.

Figure 2:
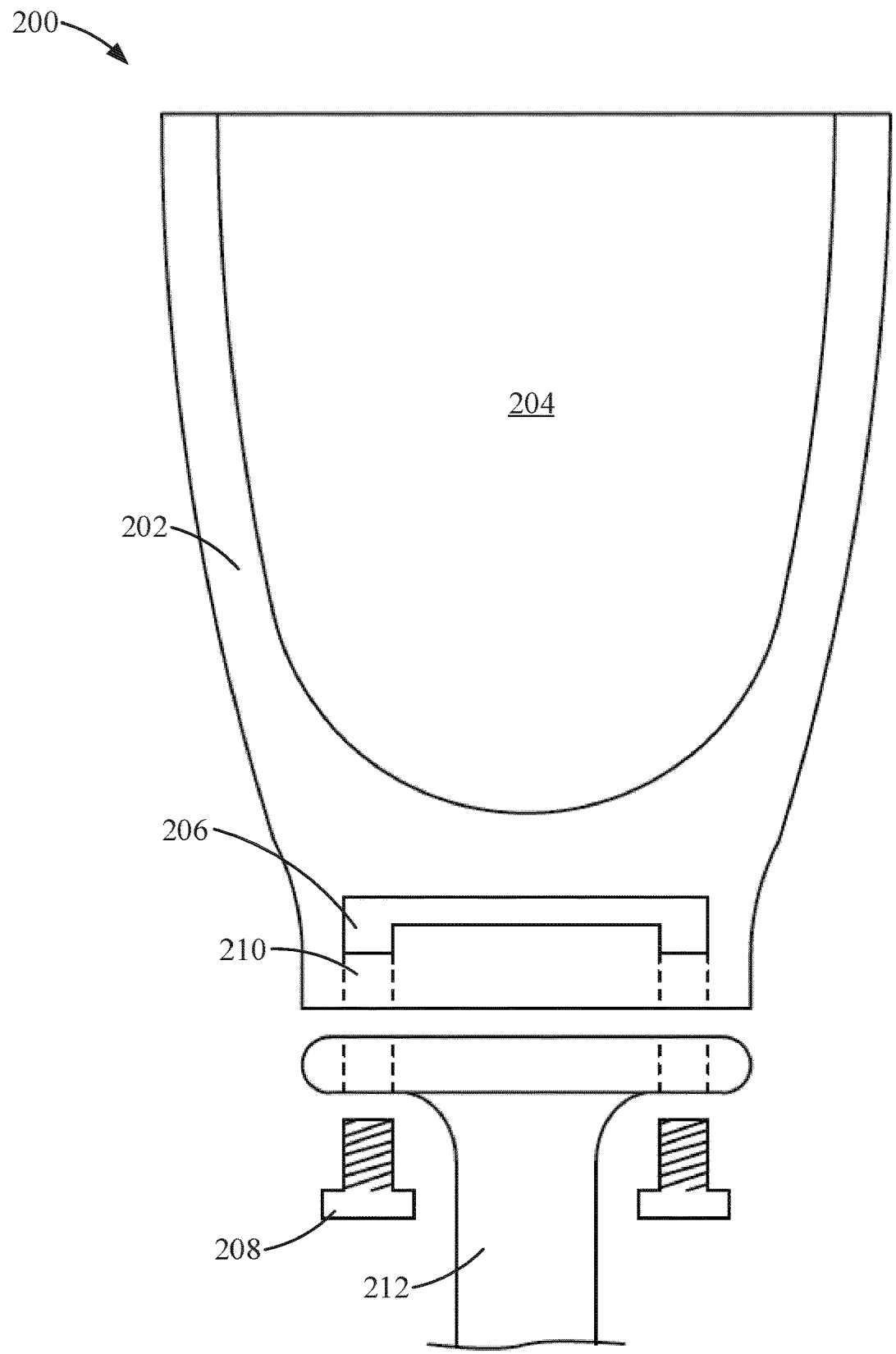
FIG. 2 shows a cross-sectional exploded view of a prosthetic device according to an example embodiment.

Referring to FIG. 2, a cross-sectional exploded view of a prosthetic device 200 is shown according to an example embodiment. The prosthetic device 200 may be, for example, a prosthetic leg. The prosthetic device 200 generally includes a socket 202 defining a cavity 204. The cavity 204 is structured to receive a residual limb of the user. The socket 202 is formed by the 3D printing process and materials described herein. The socket 202 includes a connection insert 206. The connection insert 206 is embedded in the material forming the socket 202. The connection insert 206 is embedded at a distal end of the socket 202. The connection insert 206 is configured to allow external components to be removably attached to the socket 202. Generally, the connection insert 206 includes threaded openings configured to receive the threaded fasteners 208. In its simplest form, the connection insert 206 includes a threaded fastener (e.g., a threaded nut, a threaded fastener coupled to a washer, etc.) that is embedded in the material forming the socket 202. The structure and arrangement of the connection insert 206 is described in further detail below with respect to FIGS. 3 and 4. In some arrangements, the connection insert defines a plurality of apertures and one or more connector portions fixing the positions of the apertures relative to one another. In one arrangement, the connector portions are elongated connector portions. In further arrangements, the connector portions define an "X," "U" or other shape (e.g., a hollow square or circle, etc.) that provides for significant gaps of material within a periphery defined by the plurality of apertures. The socket 202 includes through-holes 210 aligned with the threaded openings of the connection insert 206 to allow the fasteners to pass through the body of the socket 202 and engage the connection insert 206. The fasteners 208 are used to secure a pylon 212 to the socket 202. The pylon 212 may carry, for example, a prosthetic foot, a vacuum device, a controller, or the like. In an alternate arrangement, the socket 202 is divided into a first portion having the embedded connection insert 206 (i.e., a distal end of the socket 202), and a second portion including the cavity 204. In such an arrangement, the first portion may be injection molded and the second portion may be 3D printed onto the first portion. The prosthetic device 200 may have the same or similar arrangement and/or features as the prosthetic devices described in U.S. Pat. No. 9,486,334, which is herein incorporated by reference in its entirety and for all purposes.

In non-3D printed sockets for prosthetic devices (e.g., such as those described in U.S. Pat. No. 9,486,334), the pylons are attached to the socket via an external threaded adapter. The threaded adapter may be, for example, a solid disc-shaped connection insert having threaded holes to receive fasteners (e.g., similar to the fasteners 208 of the described prosthetic device). The solid disc-shaped connection insert is secured to the distal end of the socket via epoxy, covering in carbon fiber, or the like. However, 3D printed sockets formed with methods and materials described herein generally do not possess the strength to have a connection insert secured to the outside of the socket 202. If a disc-shaped connection insert is secured to the outside distal end of the socket 202, the socket may crack or brake. Further, the embedding of such a disc-shaped connection insert into the socket during the 3D manufacturing process causes the socket to crack and become unusable after a brief usage period (e.g., less than 10,000 steps taken in the prosthetic device). The cracking and breaking of the socket due to embedding an existing connection insert (i.e., the solid cylindrical disc connection insert) is often due in part to the connection insert not allowing enough 3D printed material to intertwine with the connection insert and in part to the shape of the connection insert concentrating tensile and sheer stresses at specific locations of the socket. However, these problems are addressed through unique designs of the embedded connection insert 206.

Figure 3A:
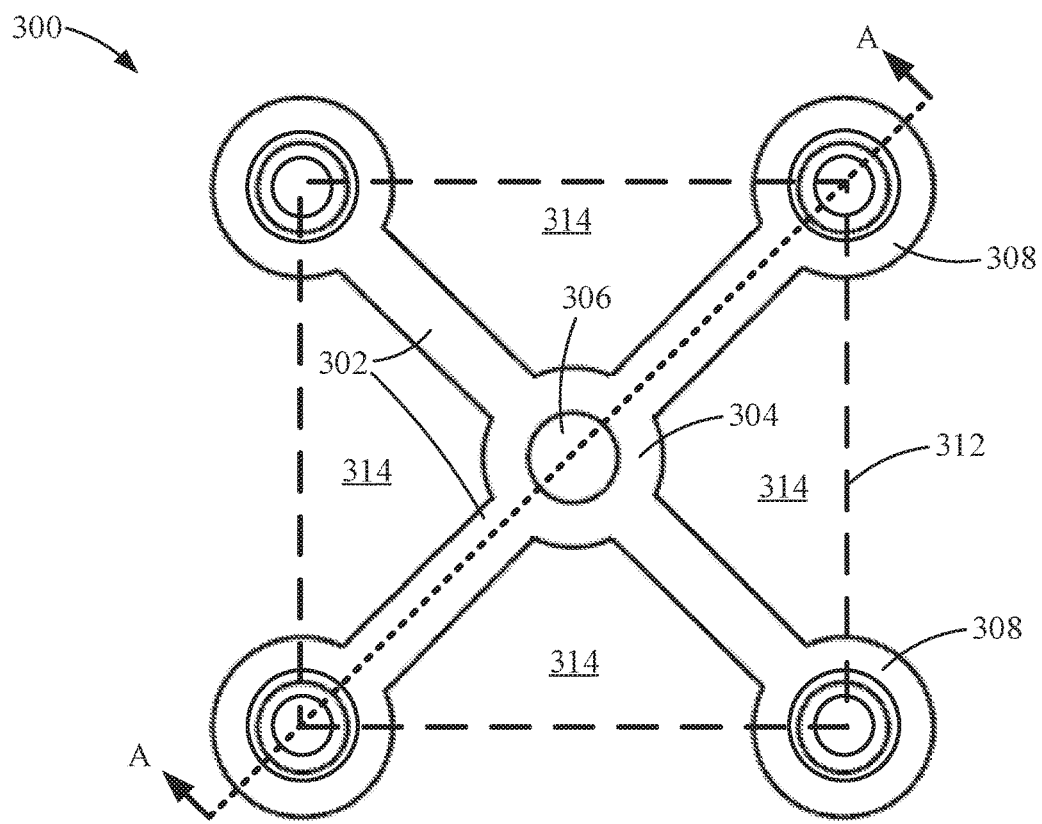
FIG. 3A shows a top view of a connection insert for a prosthetic device according to an example embodiment.
Figure 3B:
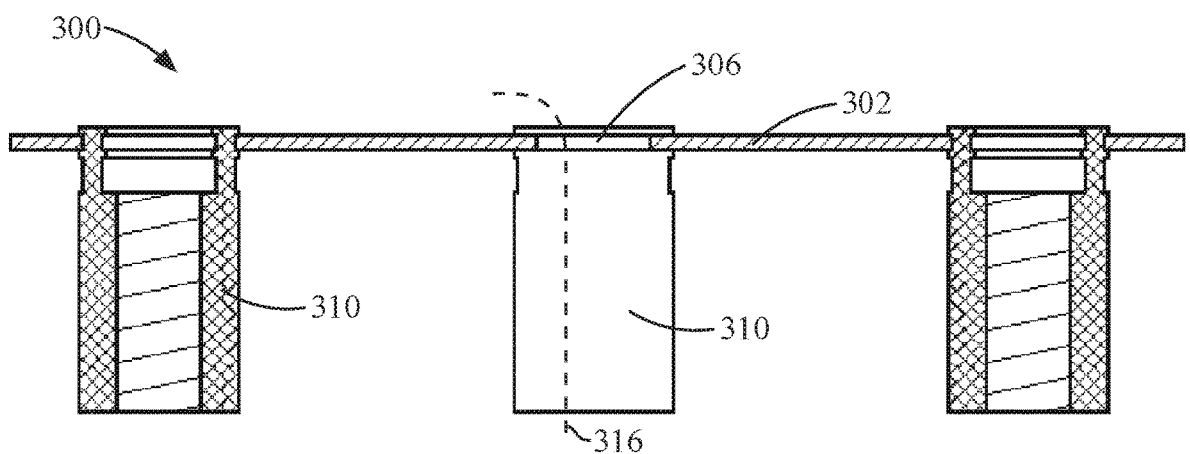
FIG. 3B shows a cross-sectional view of the connection insert of FIG. 3A.

Referring to FIGS. 3A and 3B, views of a connection insert 300 are shown according to an example embodiment. FIG. 3A shows a top view of the connection insert 300. FIG. 3B shows a close-up cross-sectional view of the connection insert 300 taken along section A-A of FIG. 3A. The connection insert 300 may be used as the connection insert 206 of the prosthetic device 200. The connection insert 300 has an overall X-shape with four arms 302 extending from a central ring 304. The central ring 304 defines a central opening 306. In some arrangements, each of the four arms 302 are the same length. Although shown as including four arms 302, any number of arms may be used in alternate arrangements. In such alternate arrangements, the arms 302 are arranged in a symmetrical manner (i.e., even circumferential spacing with respect to the central ring 304). Each of the arms 302 extends to an outer ring 308. As shown best in FIG. 3B, the outer rings 308, arms 302, and central ring 304 may be formed of a single material. For example, the outer rings 308, the arms 302, and the central ring 304 may be formed from a stamped sheet of steel, aluminum, or titanium.

The outer rings 308 define central openings that receive internally threaded fasteners 310. The internally threaded fasteners 310 may be secured in the central openings of the outer rings 308 by press fit, welding, adhesive, riveting, or the like. In some arrangements, the center points of the circular openings of the internally threaded fasteners 310 define the vertices of a square 312 (e.g., as shown in FIG. 3A). The internally threaded fasteners 310 are configured to receive the threaded fasteners 208 of the prosthetic device 200. In some arrangements, the internally threaded fasteners 310 are threaded according to the M6-1.0 threading standard. The circular shape of the outer rings 308 helps to evenly distribute the stresses (e.g., the torque, the compression) from the fasteners 208 in an even manner into the 3D printed material surrounding the outer rings 308.

The central opening 306 allows for wires or tubes (shown as element 316) to be passed through the connection insert 300. For example, in some arrangements, the prosthetic device is fitted with a vacuum system that helps retain a residual limb in the cavity 204. In such arrangements, a vacuum tube may be passed from a vacuum system external to the socket 202, through the central opening 306, and into the cavity 204. Similarly, sensor wires (e.g., vacuum sensor wires, pressure sensor wires, etc.) may be passed through the central opening 306. In some arrangements, the central opening 306 is fitted with a vacuum port or a vacuum line. In such arrangements, the socket 202 can include a 3D printed channel connecting the vacuum port or vacuum line to the cavity 204 and/or to the exterior of the socket 202 thereby eliminating the need to drill through the socket 202.

The connection insert 300 may be aligned in a particular manner during manufacturing of the prosthetic device 200. In some arrangements, the connection insert 300 is aligned such that a face of the square 312 is parallel to the ground when a user is wearing and standing with the prosthetic device 200. In such arrangements, the connection insert 300 allows for the pylon 212 to be installed such that the axial length of the pylon 212 is substantially parallel to the direction of gravity when the user is wearing and standing with the prosthetic device 200. In further arrangements, the connection insert 300 is aligned such that one of the gaps 314 between adjacent arms 302 is aligned with a front side of the socket 202. The gaps 314 extend outward beyond the periphery of the square 312. The front side of the socket 200 is worn on the same side of the residual limb as the user's knee. Accordingly, the front side of the socket 200 faces forward during a forward-facing walk by the user of the prosthetic device. The front side of the socket 202 experiences the highest amount of tensile stress during use by the user. Aligning the connection insert 300 such that one of the gaps 314 faces forward maximizes the amount of 3D printed material in the direction of the user's forward walk, which increases the strength of the socket 200 and reduces the risk of the socket 200 breaking in the area of the connection insert 300.

In an alternate arrangement, the connection insert 300 does not include the arms 302 or the central ring 304. In such an arrangement, the connection insert 300 includes four threaded fasteners 310, each coupled to a respective outer ring 308 (e.g., a circular washer). The alternative arrangement provides more flexibility in terms of placement of the threaded fasteners within the socket 202.

The overall X-shape of the connection insert 300 reduces the amount of material occupied by the connection insert 300 itself compared to a cylindrical disc having threaded holes (i.e., the externally attached connection insert described above). Accordingly, when the connection insert 300 is embedded in the socket 202 (e.g., as shown with respect to the connection insert 206), more 3D printed material can be used in the socket 202, which helps to evenly distribute the load of the user and the pylon through a greater area of the socket 202. The X-shape of the connection insert 300 achieves substantially better longevity and durability of the socket 202 compared to a cylindrical disc shaped connection inserts of prior prosthetic devices.

Figure 4A:
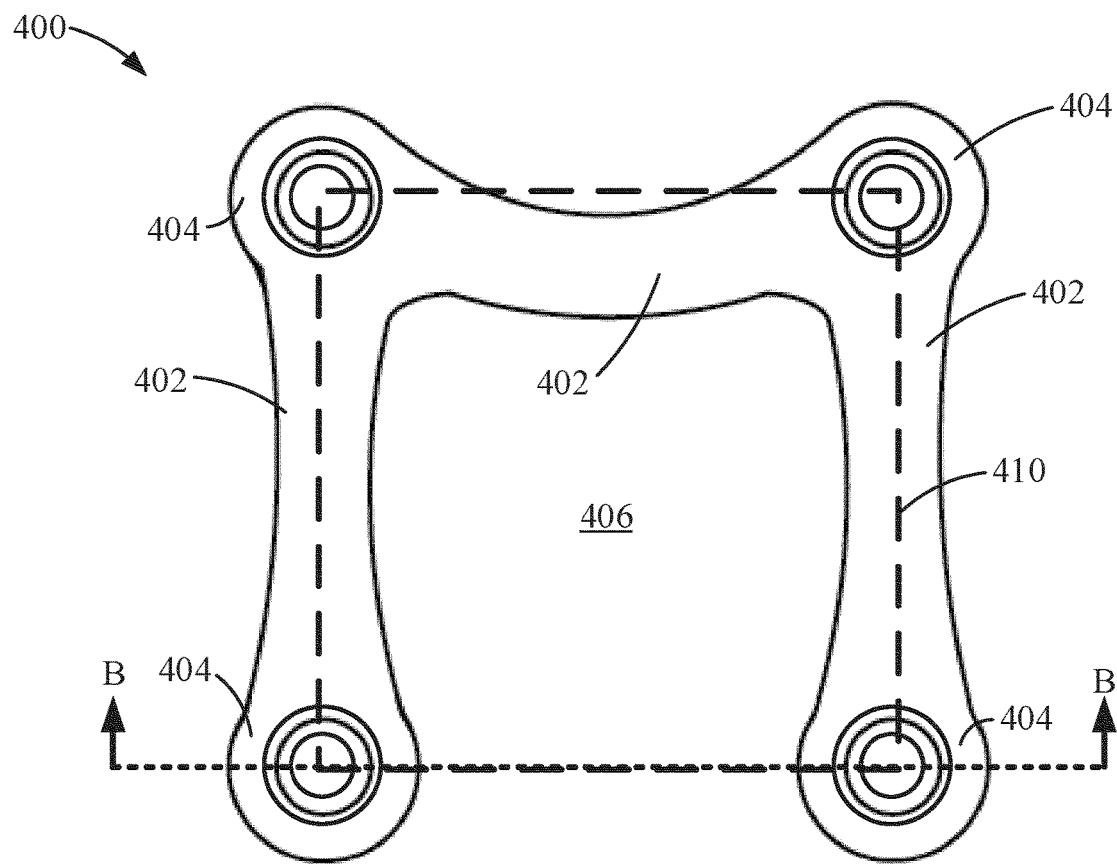
FIG. 4A shows a top view of a connection insert for a prosthetic device according to another example embodiment.
Figure 4B:
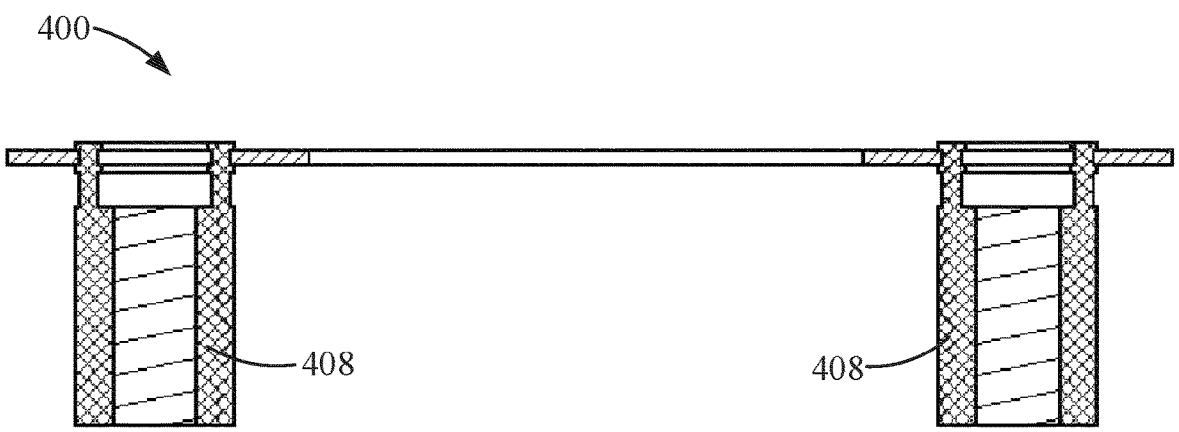
FIG. 4B shows a cross-sectional view of the connection insert of FIG. 4A.

Referring to FIGS. 4A and 4B, views of a connection insert 400 are shown according to an example embodiment. FIG. 4A shows a top view of the connection insert 400. FIG. 4B shows a close-up cross-sectional view of the connection insert 400 taken along section B-B of FIG. 4A. The connection insert 400 is similar to the connection insert 300. The connection insert 400 may be used as the connection insert 206 of the prosthetic device 200. The connection insert 400 has an overall U-shape with three arms 402 extending between and serially connecting four circular sections 404. In another arrangement, the connection insert 400 has an overall crescent shape. The circular sections 404 and the arms 402 may be formed of a single material, such as a stamped sheet of steel, aluminum, or titanium. The overall U-shape defines a central opening 406.

The circular sections 404 define central openings that receive internally threaded fasteners 408. The internally threaded fasteners 408 may be secured in the central openings of the circular sections 404 by press fit, welding, adhesive, riveting, or the like. In some arrangements, the center points of the circular openings of the internally threaded fasteners 408 define the vertices of a square 410 (e.g., as shown in FIG. 3A). The internally threaded fasteners 408 are configured to receive the threaded fasteners 208 of the prosthetic device 200. In some arrangements, the internally threaded fasteners 408 are threaded according to the M6-1.0 threading standard. The circular shape of the circular sections 404 helps to evenly distribute the stresses (e.g., the torque, the compression) from the fasteners 208 in an even manner into the 3D printed material surrounding the circular sections 404.

The central opening 406 allows for wires or tubes to be passed through the connection insert 400. For example, in some arrangements, the prosthetic device is fitted with a vacuum system that helps retain a residual limb in the cavity 204. In such arrangements, a vacuum tube may be passed from a vacuum system external to the socket 202, through the central opening 406, and into the cavity 204. Similarly, sensor wires (e.g., vacuum sensor wires, pressure sensor wires, etc.) may be passed through the central opening 406.

The overall U-shape of the connection insert 400 reduces the amount of material occupied by the connection insert 400 itself compared to a cylindrical disc having threaded holes (i.e., the externally attached connection insert described above). Accordingly, when the connection insert 400 is embedded in the socket 202 (e.g., as shown with respect to the connection insert 206), more 3D printed material can be used in the socket 202 which helps to evenly distribute the load of the user and the pylon through a greater area of the socket 202. The U-shape of the connection insert 400 achieves substantially better longevity and durability of the socket 202 compared to a cylindrical disc shaped connection inserts of prior prosthetic devices.

The connection insert 400 may be aligned in a particular manner during manufacturing of the prosthetic device 200. In some arrangements, the connection insert 400 is aligned such that a face of the square 410 is parallel to the ground when a user is wearing and standing with the prosthetic device 200. In such arrangements, the connection insert 400 allows for pylon 212 to be installed such that the axial length of the pylon 212 is substantially parallel to the direction of gravity when the user is wearing and standing with the prosthetic device 200. In further arrangements, the connection insert 400 is aligned such that open end of the U-shape is aligned with a front side of the socket 202. The front side of the socket 200 is worn on the same side of the residual limb as the user's knee. Accordingly, the front side of the socket 200 faces forward during a forward-facing walk by the user of the prosthetic device. The front side of the socket 202 experiences the highest amount of tensile stress during use by the user. Aligning the connection insert 400 such that the open end of the U-shape faces forward maximizes the amount of 3D printed material in the direction of the user's forward walk, which increases the strength of the socket 200 and reduces the risk of the socket 200 breaking in the area of the connection insert 400.

Figure 5:
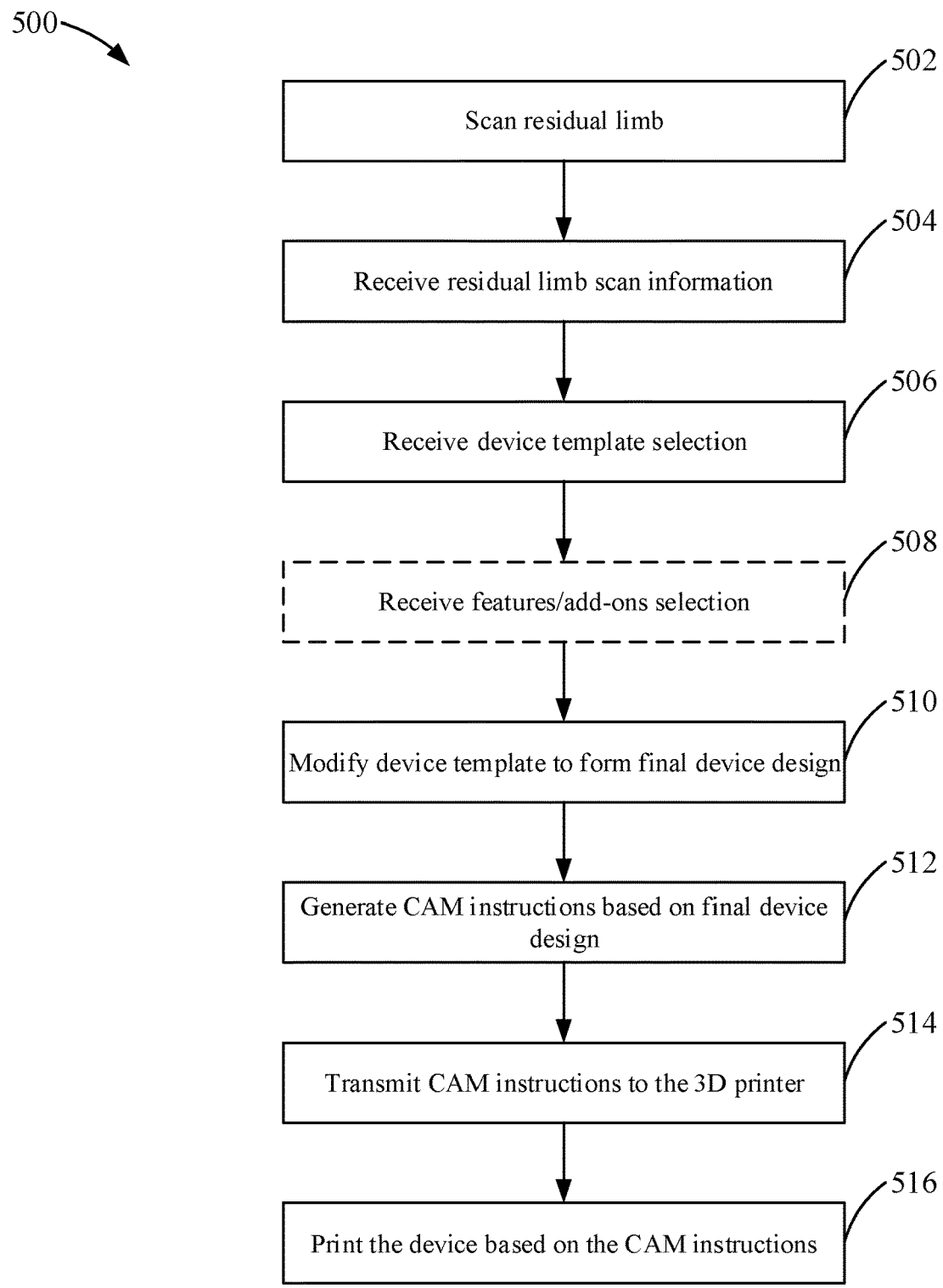
FIG. 5 shows a flow diagram of a method of making an orthotic or prosthetic device according to an example embodiment.

Referring to FIG. 5, a method 500 of making an orthotic or prosthetic device is shown according to an example embodiment. The method 500 is performed by the components of the system 100. With the exception of the scanning (at 502) and the printing (at 516), the method 500 is performed by the manufacturing computing system 104. The output of the method 500 may be, for example, the prosthetic device 200 or another orthotic or prosthetic device.

The method 500 begins when a residual limb is scanned at 502. The residual limb 108 is scanned by the 3D scanner 102. A technician secures the residual limb 108 in the correct position in the 3D scanner 102. In some arrangements, the residual limb 108 is secured in the residual limb support 110. After the residual limb 108 is secured in the correct position within the 3D scanner 102, the manufacturing computing system 104 sends a scan instruction to the 3D scanner 102 (e.g., via the scanning circuit 116). The scanning devices 112 of the 3D scanner 102 measure the shape and dimensions of the residual limb 108. The scanning devices 112 may include any of cameras, infrared cameras, lasers, ultrasonic sensors, contact sensors, or the like. In some arrangements, the scanning device 112 rotates about the residual limb 108 during 502 to measure the entirety of the portion of the residual limb 108. The 3D scanner 102 generates an output file based on the information from the scanning devices 112. In some arrangements, the output file is a three-dimensional map of the residual limb 108. The three-dimensional map may be formed by a table of three-dimensional coordinates included in the output file.

The residual limb scan information is received at 504. The manufacturing computing system 104 receives the residual limb scan information from the 3D scanner 102. In some arrangements, the scan information is stored in the output file. In such arrangements, the output file may include a three-dimensional map of the residual limb 108 and/or by a table of three-dimensional coordinates. The residual limb scan information is stored at the manufacturing computing system 104 for later use in modifying a device template (e.g., as described in further detail below with respect to 510).

A device template selection is received at 506. The device template selection is received by the manufacturing computing system 104 from a user (e.g., a prosthetic design technician) via the user interface circuit 122. The device template corresponds to a prosthetic device, an orthotic device, or another device. The device template is selected from the template database 124.

Optionally, device features or add-on selections are received at 508. The device feature and add-on selections (if any are made) are received by the manufacturing computing system 104 from the user via the user interface circuit 122. The features and add-on selections include customizations to basic devices. For example, in arrangements where the device is a prosthetic arm with fingers, the features and add-ons may include vacuum hold features, such as embedded vacuum conduits within the structure of the device, or capacitive touch fingertips made out of a different material than the standard fingertips of the device template. As another example, if the device is a prosthetic leg (e.g., the prosthetic device 200), the add-ons may include embedded support brackets (e.g., the connection inserts 206, 300, 400, etc.), internal vacuum conduits, sensor mounts, sensor wire conduits, pylon connecting holes, and the like. Other example features and add-on selections may include zippers; slots or apertures to allow for donning, doffing, and adjustment; mounting bosses; supports for tensioning devices such as straps; lacing eyelets; printed interlocking surfaces (e.g., knob and post, Velcro, etc.); and the like.

The selected device template is modified to form a final device design at 510. The manufacturing computing system 104 modifies the device template based on the shape and dimensions of the residual limb 108. In arrangements where at least one device feature or add-on selection is received at 508, the manufacturing computing system 104 further modifies the device template based on the selected features or add-ons. The manufacturing computing system 104 performs the template modification via the template customization circuit 118. In some arrangements, the user oversees the automated modification of the device template and approves the modified device template prior to certifying the modified device template as the final device design. In an alternate arrangement, steps 506 through 510 are skipped and a technician designs the device from scratch on the manufacturing computing system 104 based on the residual limb scan information. A technician (e.g., a prosthetic design technician) may use a computer aided design (CAD) software installed on the manufacturing computing system 104. The technician can interact with the CAD software via the user interface circuit 122 to create the final device design.

CAM instructions based on the final device design are generated at 512. The manufacturing computing system 104 converts the final device design into CAM instructions that are readable by the 3D printer 106. The manufacturing computing system 104 generates a file containing the CAM instructions via the printing circuit 150. The CAM instructions include printing parameters for the 3D printer 106. The printing parameters include, for example, print head printing path, printing materials, printing temperatures, and the like. In some arrangements, the CAM instructions include a break in the 3D printing of the device to allow a technician to add a component to be embedded in the printed device (e.g., to add the connection insert 206 to the socket 202 during printing). The CAM instructions are transmitted to the 3D printer at 514. The manufacturing computing system 104 transmits the file including the CAM instructions to the 3D printer 106.

The device is printed based on the CAM instructions at 516. The 3D printer 106 prints the device based on the CAM instructions. In doing so, the 3D printer 106 uses the raw materials 128 to make the device. The 3D printer can utilize multiple different materials in manufacturing the same device such that the materials can be joined without the use of adhesives or fasteners. For example, a prosthetic device can be printed that has multiple materials, including a rigid material that forms a frame section of the prosthetic device and a soft padded foam area that rests against the residual limb 108.

Figure 6:
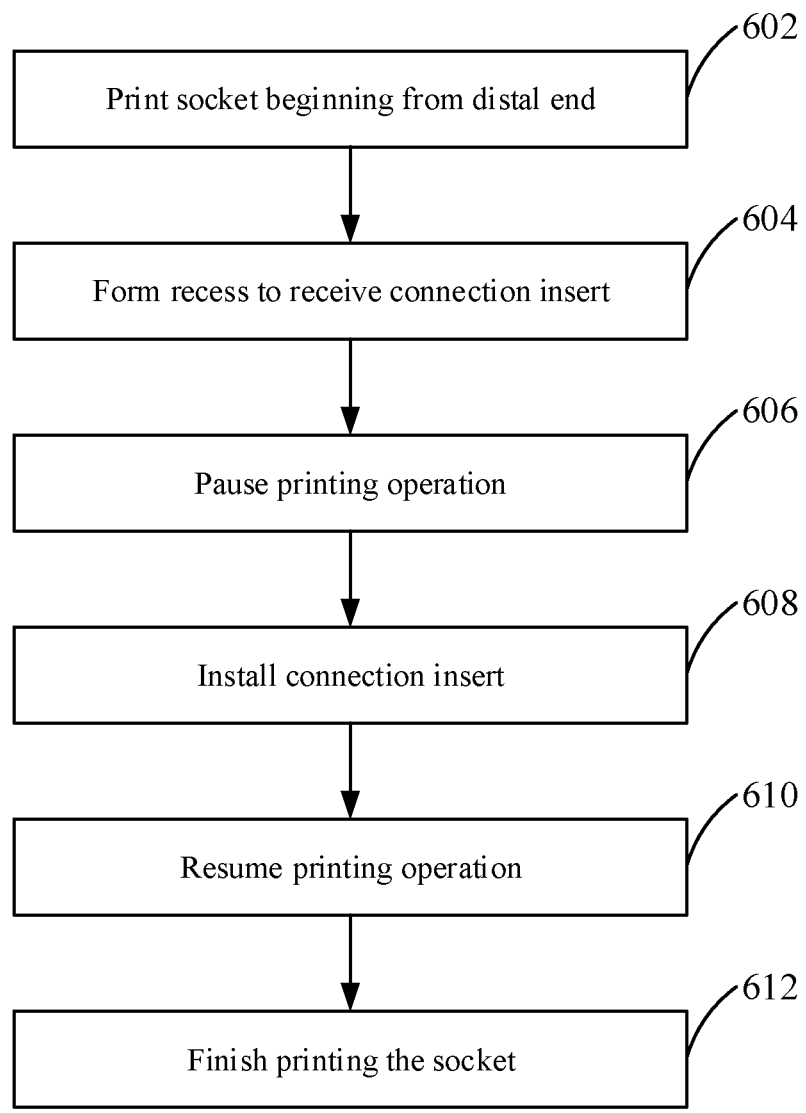
FIG. 6 shows a flow diagram of a sub-method of the method of FIG. 5.

Referring to FIG. 6, a flow diagram of a detailed description of step 516 of the method 500 is shown for printing the socket 202 of the prosthetic device 200. The 3D printer 106 begins printing the socket 202 from the distal end at 602. The distal end of the socket 202 is the end of the socket 202 that connects to the pylon 212. In some arrangements, the 3D printer prints around the through-holes 210. In other arrangements, the through-holes 210 are formed after the printing process (e.g., by drilling through the socket 202). The 3D printer 106 forms a recess to receive the connection insert (e.g., the connection insert 206, 300, or 400) at 604. The recess includes at least one channel or depression in the socket 202 that receives the connection insert.

After the socket is formed at 604, the printing operation is paused at 606. The printing operation is paused when the socket is still accessible by a technician (e.g., before the socket is printed over with material by the 3D printer 106). The connection insert is installed at 608. A technician installs the connection insert into the socket 202. After the connection insert is installed, the printing operation is resumed at 610. The 3D printer 106 continues to print the socket 202, including laying material over and around the connection insert thereby securing and embedding the connection insert in the socket 202. The socket is finished at 612. The 3D printer 106 continues printing the socket until the socket 202 is finished.

In an alternative arrangement of the step 516 of the method 500, the recess formed at 604 extends to an exterior surface of the socket 202 and forms a "key" slot. In such an arrangement, the connection insert can be inserted into the socket 202 after the printing operation has concluded through the exposed key slot. Accordingly, in the alternative arrangement, the pausing of the printing operation 606 is skipped, and the connection insert is installed after 612 (i.e., after the socket has finished printing). In some arrangements, the remaining empty space formed by the slot after inserting the connection insert is inserted into the slot is filled with a filler material (e.g., epoxy, etc.).

The above-described 3D printing and additive manufacturing system and process allow for prosthetic devices and orthotic devices having unique integral features. For example, devices can be printed that have slots or apertures to allow for donning, doffing, and adjustment (e.g., printed zippers, printed mounting bosses, printed supports for tensioning devices and straps). The printing operations can be paused (e.g., in a similar manner as described above with respect to installing the connection insert) to add separate metal components, such as rods or triangle style strap hinges directly into printed mounts or bosses on the surface of a printed part. In further arrangements, parts can be printed with eyelets positioned horizontally or vertically with reference to the surface for lacing and/or with reel lacing connections. Devices can be printed having integral mounting or adjustment straps of the same or different material as the device. The straps can be printed with belt type holes and fasteners or with stepped or ratchet connections. Strap management features (e.g., strap containment devices) can also be printed directly into the device.

3D printed devices can be printed to include mating surface interlocks on selective areas instead of Velcro or belt tensioners that are conducive to 3D type printing. For example, knob and post connectors can be printed. In this arrangement, a post is printed perpendicular to the surface that has a sphere, or most of a sphere, printed on the top of the post. This would resemble a knob. These are printed in arrays on the surfaces to be joined. The spheres of one surface would snap into a group of four spheres on the other surface. Many of these connections would be made to provide the strength or strap management required. The post may be 0.1 inches tall and have a thickness of approximately 0.050 inches, while the sphere can be 0.1 inches in diameter and rest on top of the post. The printed array can have the posts spaced at 0.150 inches on its x and y axis. This would allow a knob from a parallel surface to enter a group of four knobs and distort them slightly or compress their knobs, so the intruding knob goes between and below the group of four. The pressure required to insert and release would be determined by material durometer, material surface, sticky or slippery surface, size of knobs, spacing of the knobs, and shape of the knobs (e.g., knobs having a shape other than spheres). For example, hemispheres for the knobs would allow the radius surfaces of the hemisphere to allow easier insertion then the flats of the bottoms of the hemispheres to be against each other and provide more effort to release than insert. Other mating surfaces can include dovetails, tapered bosses, pegs, or other printed mechanical interlocking features, to join multiple materials, or join multiple materials that are incompatible chemically, and would otherwise delaminate. The use of the mating surfaces can be used to prevent two or more materials from separating during dynamic operation of the device, to provide anti-torquing or anti-rotation between the multiple materials printed within the device, to allow for structural attachment components to connect the body of the printed device to other components such as pyramid or pylon adapters, or wrist to hand connectors.

The 3D printing allows for varied use of the same material and the use of multiple materials that form an integral device. For example, 3D printing allows for the placement of two or more materials on the same layer throughout the device during the same print cycle. For example, materials of different hardness can be printed in the same cycle (e.g., where the padded foam area is ultimately placed against patient's skin), stiffening materials can be embedded to provide extra rigidity and restrict movement, weight saving materials can be used where appropriate (e.g., the use of different infills), and the like. This may be used, for example, to print a prosthetic hand connection device that has a compliant or flexible area printed inline through the wrist to a rigid area proximal to the wrist which is rigid for connection to the patient. The various portions can be printed during the same print cycle, which allows flexion and extension along with pronation and supination. As another example, terrain compliance on devices can be added (e.g., the sole of an artificial foot can consist of variable thickness and variable durometer materials, all printed during the same print cycle). As a further example, parts can be printed using two different materials having two different durometers, such as a first material that is harder and more rigid than a second material (e.g., an elastomer material), to provide for areas of devices that can rotate, twist, or flex, which may provide a more comfortable fit to a user of the prosthetic or orthotic device. The use of different materials also allows for the printing of springs with 3D printed material (e.g., plastic coil or leaf springs for compression or expansion applications between items that need to be separated with a spring connection, articulations or "living hinges" within the device without separating the device in to multiple components or adding additional external hardware, and the like).

The use of the above-described 3D printing systems and methods can also provide for devices with integral voids in the material (e.g., formed without removing materials). For example, devices can be printed with integral holes, slots, cutouts, embosses, debosses, or other blind recesses (areas that do not go completely through the device), other items for secondary and external component attachment, void areas (e.g., to reduce weight or allow ventilation openings), non-solid infills that are offset to allow a cushioning effect until a certain parameter, such as force, is achieved then allow a further movement by collapsing or otherwise compressing, and the like.

Similarly, the 3D printed infill ratio of a device can be varied at different portions of the device. For example, a first portion of the device can utilize a 25% infill to provide weight savings, whereas a second portion of the device can utilize a 100% infill to provide greater strength. The use of a higher infill (e.g., 100% infill instead of 25% infill) allows for better modification of the device after printing. For example, a clinician can use heat to modify a portion of a device printed with 100% infill (e.g., to the heated portion) to, for example, create a brim on the edge of a socket. Whereas the reshaping via heat is more difficult for areas with 25% infill because there is less material to modify and the risk of damaging the device is increased.

Further, the use of the above-described systems and methods allows for unique electronic features to be integrated directly into the 3D printed devices. For example, devices can be printed with electrically conductive materials along with electrically isolated materials to create devices that contain printed wires, traces, or other electrically conductive areas, that are on the surface or embedded within the device (e.g., to communicate patient signals, provide power to motors, provide power to cooling devices, provide patient neuro-stimulation, function as battery or power supply connections, etc.). As another example, devices can be printed with electrically conductive materials on the surface or embedded in the interior surfaces to provide Radio Frequency Interference (RFI) shielding of electronic devices such as sensors, amplifiers or other components that require interference shielding, to allow for interaction with capacitive touch screen devices (e.g., smartphones, tablets, ATMs, etc.) by printing the conductive surfaces on fingertips of a prosthetic hand.

Other features enabled by the above-described systems and methods include the integral waterproofing of portions of the devices through the use of different materials, the integration of covers to protect components, the printing of channels or tubes within the devices, and the like.

Although the example device described in detail herein relates to a prosthetic limb, other improved prosthetic and orthotic devices can be manufactured by the systems and methods described herein. For example, the same principles can be applied to the design and manufacture of cranial remolding orthosis (CRO) devices. Currently, CRO devices are fabricated manually. For example, current CRO devices may be manufactured by manually carving a foam block to form a model of a patient, coating the foam block with plastic, and manual trimming of the plastic. The existing manner of creating a CRO device is labor intensive and time consuming. Through the manufacturing systems and methods described herein, the process is simplified and the device is improved. The technician can leverage the 3D scanner 102 and the manufacturing computing system 104 to create an accurate 3D CAD model of the CRO device for a given patient. Any trimming of materials (e.g., for a better fit, to add ventilation holes), modification of material thickness can be performed on the CAD model instead of the actual device, thereby reducing time and risk of damage to the device. Once the CAD model is finalized, the 3D printer 106 can be configured to print the CRO device. The 3D printer 106 can print multiple and connected materials at the same time (e.g., the rigid outer frame of the CRO device and the padded inner foam), thereby reducing assembly time for the technician. Similar processes to the above-described one with respect to the CRO device can be directly applied to other devices, including: ankle foot orthosis (AFO), transmetatarsal orthosis (TMO), foot orthotics (FO), diabetic inserts, and body jackets utilized for spine correction, such as for patients with scoliosis, and the like.

In another arrangement, the above-described systems and methods can be used to create upper extremity prosthetic devices, such as prosthetic arms. In such arrangements, the described connection inserts can be embedded in 3D printed sockets that receive residual arms in the same manner described above. The connection inserts can be structured to receive devices other than a pylon, such as a prosthetic hand, and can include openings to receive sensor wires that allow the users to control the operation of various motors and actuators in the attached prosthetic hand.

The above-described systems and methods allow for prosthetic and orthotic devices to be manufactured as a single piece with integrated features. For example, the devices may include rigid materials (e.g., hard plastics or metals) and less rigid materials (e.g., soft foams and rubbers). Additionally, the devices may include integrated vacuum channels within the frame, integrated closure mechanisms (e.g., 3D printed zippers, 3D printed knob and post attachments, integrated lace eyelets, 3D printed snaps, 3D printed dovetailing or mechanical interlocks, etc.), capacitive touch materials that connect the residual limb 108 to an exterior of the prosthetic device (e.g., to a fingertip), 3D printed living hinges, integrated radio frequency interference shielding that protects electronic devices of the prosthetic device, integrated water proofing components. Additionally, the above-described systems and methods reduce manufacturing times and costs for prosthetic and orthotic devices.

It should be noted that any use of the term "example" herein to describe various embodiments is intended to indicate that such embodiments are possible examples, representations, and/or illustrations of possible embodiments (and such term is not intended to connote that such embodiments are necessarily extraordinary or superlative examples).

The terms "coupled" and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

It should be understood that no claim element herein is to be construed under the provisions of 35 U.S.C. § 112(f), unless the element is expressly recited using the phrase "means for."

As used herein, the term "circuit" may include hardware structured to execute the functions described herein. In some embodiments, each respective "circuit" may include machine-readable media for configuring the hardware to execute the functions described herein. The circuit may be embodied as one or more circuitry components including, but not limited to, processing circuitry, network interfaces, peripheral devices, input devices, output devices, sensors, etc. In some embodiments, a circuit may take the form of one or more analog circuits, electronic circuits (e.g., integrated circuits (IC), discrete circuits, system on a chip (SOCs) circuits, etc.), telecommunication circuits, hybrid circuits, and any other type of "circuit." In this regard, the "circuit" may include any type of component for accomplishing or facilitating achievement of the operations described herein. For example, a circuit as described herein may include one or more transistors, logic gates (e.g., NAND, AND, NOR, OR, XOR, NOT, XNOR, etc.), resistors, multiplexers, registers, capacitors, inductors, diodes, wiring, and so on).

The "circuit" may also include one or more processors communicatively coupled to one or more memory or memory devices. In this regard, the one or more processors may execute instructions stored in the memory or may execute instructions otherwise accessible to the one or more processors. In some embodiments, the one or more processors may be embodied in various ways. The one or more processors may be constructed in a manner sufficient to perform at least the operations described herein. In some embodiments, the one or more processors may be shared by multiple circuits (e.g., circuit A and circuit B may comprise or otherwise share the same processor which, in some example embodiments, may execute instructions stored, or otherwise accessed, via different areas of memory). Alternatively or additionally, the one or more processors may be structured to perform or otherwise execute certain operations independent of one or more co-processors. In other example embodiments, two or more processors may be coupled via a bus to enable independent, parallel, pipelined, or multi-threaded instruction execution. Each processor may be implemented as one or more general-purpose processors, application specific integrated circuits (ASICs), field programmable gate arrays (FPGAs), digital signal processors (DSPs), or other suitable electronic data processing components structured to execute instructions provided by memory. The one or more processors may take the form of a single core processor, multi-core processor (e.g., a dual core processor, triple core processor, quad core processor, etc.), microprocessor, etc. In some embodiments, the one or more processors may be external to the apparatus, for example the one or more processors may be a remote processor (e.g., a cloud based processor). Alternatively or additionally, the one or more processors may be internal and/or local to the apparatus. In this regard, a given circuit or components thereof may be disposed locally (e.g., as part of a local server, a local computing system, etc.) or remotely (e.g., as part of a remote server such as a cloud based server). To that end, a "circuit" as described herein may include components that are distributed across one or more locations.

An exemplary system for implementing the overall system or portions of the embodiments might include a general purpose computing computers in the form of computers, including a processing unit, a system memory, and a system bus that couples various system components including the system memory to the processing unit. Each memory device may include non-transient volatile storage media, non-volatile storage media, non-transitory storage media (e.g., one or more volatile and/or non-volatile memories), etc. In some embodiments, the non-volatile media may take the form of ROM, flash memory (e.g., flash memory such as NAND, 3D NAND, NOR, 3D NOR, etc.), EEPROM, MRAM, magnetic storage, hard discs, optical discs, etc. In other embodiments, the volatile storage media may take the form of RAM, TRAM, ZRAM, etc. Combinations of the above are also included within the scope of machine-readable media. In this regard, machine-executable instructions comprise, for example, instructions and data which cause a general purpose computer, special purpose computer, or special purpose processing machines to perform a certain function or group of functions. Each respective memory device may be operable to maintain or otherwise store information relating to the operations performed by one or more associated circuits, including processor instructions and related data (e.g., database components, object code components, script components, etc.), in accordance with the example embodiments described herein.

It should also be noted that the term "input devices," as described herein, may include any type of input device including, but not limited to, a keyboard, a keypad, a mouse, joystick or other input devices performing a similar function. Comparatively, the term "output device," as described herein, may include any type of output device including, but not limited to, a computer monitor, printer, facsimile machine, or other output devices performing a similar function.

The embodiments described herein have been described with reference to drawings. The drawings illustrate certain details of specific embodiments that implement the systems, methods and programs described herein. However, describing the embodiments with drawings should not be construed as imposing on the disclosure any limitations that may be present in the drawings.

It should be noted that although the drawings herein may show a specific order and composition of method steps, it is understood that the order of these steps may differ from what is depicted. For example, two or more steps may be performed concurrently or with partial concurrence. Also, some method steps that are performed as discrete steps may be combined, steps being performed as a combined step may be separated into discrete steps, the sequence of certain processes may be reversed or otherwise varied, and the nature or number of discrete processes may be altered or varied. The order or sequence of any element or apparatus may be varied or substituted according to alternative embodiments. Accordingly, all such modifications are intended to be included within the scope of the present disclosure as defined in the appended claims. Such variations will depend on the machine-readable media and hardware systems chosen and on designer choice. It is understood that all such variations are within the scope of the disclosure. Likewise, software and web implementations of the present disclosure could be accomplished with standard programming techniques with rule based logic and other logic to accomplish the various database searching steps, correlation steps, comparison steps and decision steps.

It is important to note that the construction and arrangement of the various example embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. For example, elements shown as integrally formed may be constructed of multiple parts or elements, the position of elements may be reversed or otherwise varied, and the nature or number of discrete elements or positions may be altered or varied. Additionally, features from particular embodiments may be combined with features from other embodiments as would be understood by one of ordinary skill in the art. Other substitutions, modifications, changes and omissions may also be made in the design, operating conditions and arrangement of the various example embodiments without departing from the scope of the present disclosure.

The foregoing description of embodiments has been presented for purposes of illustration and description. It is not intended to be exhaustive or to limit the disclosure to the precise form disclosed, and modifications and variations are possible in light of the above teachings or may be acquired from this disclosure. The embodiments were chosen and described in order to explain the principals of the disclosure and its practical application to enable one skilled in the art to utilize the various embodiments and with various modifications as are suited to the particular use contemplated. Other substitutions, modifications, changes and omissions may be made in the design, operating conditions and arrangement of the embodiments without departing from the scope of the present disclosure as expressed in the appended claims.

What is claimed is:

1. A prosthetic device comprising:
   a socket defining a cavity configured to receive a residual limb of a user, wherein the socket is formed by a three-dimensional printing process;
   a pylon coupled to the distal end of the socket by a threaded fastener; and
   a connection insert within the socket, the connection insert comprising an internally threaded fastener aligned with a through hole in the socket, wherein the internally threaded fastener is structured to receive the threaded fastener thereby securing the pylon to the socket;
   wherein the socket formed by the three-dimensional printing process extends along an entirety of a top surface of the connection insert;
   wherein at least one of a vacuum line or a wire passes from an exterior of the socket, through a central opening of the connection insert, and into the cavity defined by the socket.

2. The device of claim 1, wherein the connection insert is comprised of metal, and wherein the socket is comprised of three-dimensionally printed plastic.

3. The device of claim 1, wherein the connection insert is not disc-shaped.

4. A prosthetic device comprising:
   a socket defining a cavity configured to receive a residual limb of a user, wherein the socket is formed by a three-dimensional printing process;
   a pylon coupled to the distal end of the socket by a threaded fastener; and
   a connection insert within the socket, the connection insert comprising an internally threaded fastener aligned with a through hole in the socket, wherein the internally threaded fastener is structured to receive the threaded fastener thereby securing the pylon to the socket;
   wherein the socket formed by the three-dimensional printing process extends along an entirety of a top surface of the connection insert;
   wherein the connection insert is not disc-shaped;
   wherein the internally threaded fastener is a first internally threaded fastener, wherein the connection insert further comprises a second internally threaded fastener, a third internally threaded fastener, and a fourth internally threaded fastener.

5. The device of claim 4, wherein each of the first, second, third, and fourth internally threaded fasteners define a circular opening having a center point, wherein the first, second, third, and fourth internally threaded fasteners are positioned such that the four center points define the vertices of a square.

6. The device of claim 4, wherein the connection insert has an overall X-shape.

7. The device of claim 4, wherein the connection insert has an overall U-shape.

8. A prosthetic device comprising:
- a socket defining a cavity configured to receive a residual limb of a user, wherein the socket is formed by a three-dimensional printing process;
- a pylon coupled to the distal end of the socket by a threaded fastener; and
- a connection insert provided within the socket, the connection insert comprising a connection insert body and a plurality of internally threaded fasteners coupled to the connection insert body, wherein the connection insert body is configured to receive the threaded fastener thereby coupling the pylon to the socket;
- wherein the socket formed by the three-dimensional printing process extends along an entirety of a top surface of the connection insert;
- wherein the connection insert has an overall X-shape.

9. The prosthetic device of claim 8, wherein the connection insert is not disc-shaped.

10. A prosthetic device comprising:
- a socket defining a cavity configured to receive a residual limb of a user, wherein the socket is formed by a three-dimensional printing process;
- a pylon coupled to the distal end of the socket by a threaded fastener; and
- a connection insert provided within the socket, the connection insert comprising a connection insert body and a plurality of internally threaded fasteners coupled to the connection insert body, wherein the connection insert body is configured to receive the threaded fastener thereby coupling the pylon to the socket;
- wherein the socket formed by the three-dimensional printing process extends along an entirety of a top surface of the connection insert; and
- wherein the plurality of internally threaded fasteners comprise:
  - a first internally threaded fastener coupled to the connection insert body;
  - a second internally threaded fastener coupled to the connection insert body;
  - a third internally threaded fastener coupled to the connection insert body; and
  - a fourth internally threaded fastener coupled to the connection insert body.

11. The prosthetic device of claim 10, wherein each of the first, second, third, and fourth internally threaded fasteners define a circular opening having a center point, wherein the first, second, third, and fourth internally threaded fasteners are positioned such that the four center points define the vertices of a square.

* * * * *